United States Patent [19]
Wang et al.

[11] Patent Number: 6,111,014
[45] Date of Patent: Aug. 29, 2000

[54] FILM OF MONOMER-GRAFTED POLYOLEFIN AND POLY(ETHYLENE OXIDE)

[75] Inventors: James Hongxue Wang, Appleton, Wis.; David Michael Schertz, Roswell, Ga.

[73] Assignee: Kimberly-Clark Worldwide, Inc., Neenah, Wis.

[21] Appl. No.: 09/094,887

[22] Filed: Jun. 15, 1998

Related U.S. Application Data

[63] Continuation-in-part of application No. 08/813,571, Mar. 6, 1997, abandoned
[60] Provisional application No. 60/034,616, Dec. 31, 1996.

[51] Int. Cl.[7] .................................................. C08L 51/06
[52] U.S. Cl. ......................................... 525/64; 525/187
[58] Field of Search ....................................... 525/187, 64

[56] References Cited

U.S. PATENT DOCUMENTS

| | | | |
|---|---|---|---|
| 3,323,978 | 6/1967 | Rasmussen | 161/169 |
| 3,539,666 | 11/1970 | Schirmer | 264/51 |
| 3,717,541 | 2/1973 | Schirmer | 161/169 |
| 3,833,708 | 9/1974 | Miller et al. | 264/344 |
| 3,935,141 | 1/1976 | Potts et al. | 260/23 H |
| 3,954,928 | 5/1976 | Omori et al. | 264/51 |
| 4,018,729 | 4/1977 | Faucher et al. | 260/17 R |
| 4,080,405 | 3/1978 | Agouri et al. | 260/878 R |
| 4,186,233 | 1/1980 | Krajewski et al. | 428/213 |
| 4,415,691 | 11/1983 | Allen et al. | 524/114 |
| 4,590,227 | 5/1986 | Nakamura et al. | 525/54.31 |
| 4,868,222 | 9/1989 | Chau et al. | 521/61 |
| 5,095,619 | 3/1992 | Davis et al. | 30/40 |
| 5,288,532 | 2/1994 | Juhl et al. | 525/187 |
| 5,300,574 | 4/1994 | Bacskai | 525/181 |
| 5,367,003 | 11/1994 | Petcavich | 523/124 |
| 5,369,168 | 11/1994 | Famili et al. | 525/57 |
| 5,391,423 | 2/1995 | Wnuk et al. | 428/217 |
| 5,395,308 | 3/1995 | Fox et al. | 604/15 |
| 5,415,905 | 5/1995 | Middlesworth et al. | 528/35.7 |
| 5,417,679 | 5/1995 | Toms et al. | 604/370 |
| 5,429,874 | 7/1995 | VanPutte | 428/522 |
| 5,446,100 | 8/1995 | Durrance et al. | 525/221 |
| 5,464,687 | 11/1995 | Sheth | 428/286 |
| 5,468,259 | 11/1995 | Sheth et al. | 8/497 |
| 5,489,470 | 2/1996 | Noda | 428/286 |
| 5,498,692 | 3/1996 | Noda | 528/361 |
| 5,498,785 | 3/1996 | Wang et al. | 525/371 |
| 5,509,913 | 4/1996 | Yeo | 604/364 |
| 5,532,066 | 7/1996 | Latiolais et al. | 428/483 |
| 5,540,663 | 7/1996 | Kroner et al. | 428/221 |
| 5,549,791 | 8/1996 | Herron et al. | 162/157.6 |
| 5,641,562 | 6/1997 | Larson et al. | 442/394 |
| 5,700,872 | 12/1997 | Wang et al. | 525/187 |
| 5,912,076 | 6/1999 | Wang et al. | 525/187 |
| 5,916,969 | 6/1999 | Wang et al. | 525/187 |

FOREIGN PATENT DOCUMENTS

| | | |
|---|---|---|
| A-52355/93 | 3/1994 | Australia . |
| 0 184 440 | 6/1986 | European Pat. Off. . |
| 0296355 A2 | 12/1988 | European Pat. Off. . |
| 49-126742 | 12/1974 | Japan . |
| 61-272217 | 12/1986 | Japan . |
| 2 295 553 | 6/1996 | United Kingdom . |
| WO 94/00163 | 1/1994 | WIPO . |
| WO 94/00293 | 1/1994 | WIPO . |
| WO 95/11929 | 4/1995 | WIPO . |
| WO 95/20614 | 8/1995 | WIPO . |
| WO 95/20615 | 8/1995 | WIPO . |
| WO 95/20621 | 8/1995 | WIPO . |
| WO 95/23249 | 8/1995 | WIPO . |
| WO 95/23250 | 8/1995 | WIPO . |
| WO 96/21057 | 7/1996 | WIPO . |
| WO 96/21475 | 8/1996 | WIPO . |

OTHER PUBLICATIONS

Bartczak, Z. and A. Galeski, "Changes in Interface Shape Druing Crystallization in Two–Component Polymer Systems", Polymer, 1986, vol. 27, Apr., pp. 544–548.

Mortensen, Kell, "Phase Behavior of Poly(propylene Oxide-)–Poly(ethylene oxide)–Poly(propylene oxide) Triblock Copolymer Melt and Aqueous Solutions", Macromolecules, vol. 27, No. 20, 1994, pp. 5654–5666.

Song, Z. and W.E. Baker, "Melt Grafting of T–Butylaminoehtyl Methacrylate Onto Polyethylene," Polymer, 1992, vol. 33, No. 15, pp. 3266–3273.

Tang, Tao and Baotong Huang, "Compatibilization of Polypropylene/Poly (Ethylene Oxide) Blends and Crystallization Behavior of the Blends," Journal of Polymer Science: Part B: Polymer Physics, vol. 32, (1994), pp. 1991–1998.

*Primary Examiner*—Robert E. Sellers
*Attorney, Agent, or Firm*—Jerry F. Janssen; Mark L. Davis; Thomas D. Wilhelm

[57] ABSTRACT

The invention provides a water degradable polyolefin-containing film having greater than about 55 weight percent of a modified polyolefin and less than about 45 weight percent of unmodified poly(ethylene oxide). The polyolefin is modified by grafting thereto a monomer selected from 2-hydroxyethyl methacrylate and polyethylene glycol ethyl ether methacrylate in an amount ranging between about 0.1 weight percent and about 30 weight percent, based on the total weight of the polymer blend. The polyolefin-containing film, when immersed in water for about 30 seconds, loses at least 10% in two or more of the tensile properties: percent strain-to-break, peak stress, energy-to-break and modulus when compared to the dry or pre-immersion values. Also provided are flushable personal care articles such as infant diapers, feminine hygiene napkins, and adult incontinence garments having a backing or barrier layer comprising a water degradable polyolefin-containing film of the invention.

18 Claims, No Drawings

6,111,014

FILM OF MONOMER-GRAFTED POLYOLEFIN AND POLY(ETHYLENE OXIDE)

CROSS-REFERENCE TO RELATED APPLICATIONS

This application is a continuation-in-part of application Ser. No. 08/813,571 filed Mar. 6, 1997, abandoned, which, claims priority from Provisional Application Serial No. 60/034,616 filed Dec. 31, 1996, the disclosures of which are incorporated herein by reference.

FIELD OF THE INVENTION

The present invention relates to a water-degradable or flushable polyolefin-containing film. More particularly, the present invention relates to a water-degradable or flushable polyolefin-containing film having greater than about 55 weight percent of a modified polyolefin and less than about 45 weight percent of poly(ethylene oxide).

BACKGROUND OF THE INVENTION

Such articles typically have some portion, usually the backing layer, liner, or baffle constructed of a liquid repellent film material. This repellent material is appropriately constructed to minimize or prevent the exudation of the absorbed liquid from the article and to obtain greater utilization of the absorbent capacity of the product. The liquid repellent film commonly used includes plastic materials such as polyethylene films and the like.

Although such products are relatively inexpensive, sanitary and easy to use, disposal of a soiled product is not without its problems. With greater interest being placed in protecting the environment today, there is a need to develop materials that are more compatible with the existing and developing waste disposal technologies while still delivering performance consumers have come to expect. An ideal disposal alternative would be to use municipal sewage treatment and private residential septic systems. Products suited for disposal in sewage systems can be flushed down a convenient toilet and are termed "flushable." While flushing such articles would be convenient, the liquid repellent material which normally does not disintegrate in water tends to plug toilets and sewer pipes. It therefore becomes necessary, although undesirable, to separate the barrier film material from the absorbent article prior to flushing.

In addition to the article itself, typically the packaging in which the disposable article is distributed is also made from a water resistant material. Water resistivity is necessary to prevent the degradation of the packaging from environmental conditions and to protect the disposable articles therein. Although this packaging may be safely stored with other refuse for commercial disposal, and especially in the case of individual packaging of the products, it is often more convenient to dispose of the packaging in the toilet with the discarded disposable article. However, in the cases where such packaging is composed of a water resistant material, plugging of the drains to the toilet typically results.

Desirably, a commercial, flushable product should be relatively responsive to water and be transportable in a sewer system. Commercially available water-soluble polymers, such as polyethylene oxide (PEO), polyvinyl alcohol (PVOH), acrylamide polymers, acrylic acid-based polymers, and cellulose derivatives, possess the desired characteristics for flushability, such as water solubility and/or water dispersibility. However, due to their in-use degradability and storage degradation, these materials function poorly as components in personal care products. Other disadvantages are that these polymers are difficult to process and are substantially more expensive than polyolefins.

The requirements for a functional and flushable product provide a substantial challenge in finding suitable materials with the desired properties. In an attempt to overcome the flushability problem of a water resistant film the prior art has modified the water resistant polymer. One of the more useful ways of modifying polymers involves blending them with other polymers of different structures and properties.

Polymer blends of polyolefins and poly(ethylene oxide) have been shown to be water modifiable at expectedly low weight % polyolefin levels. Such blends would be anticipated to be flushable when exposed to water in a toilet but do not possess the dry mechanical properties required for functionality in use. Moreover, the high content of poly (ethylene oxide) makes such materials prohibitively expensive for use in a disposable personal hygiene article such as a sanitary napkin, diaper and the like. Polymer blends of polyolefins and poly(ethylene oxide) containing greater than about weight percent of polyolefin are generally water resistant and are not water modifiable.

In view of the problems of the prior art, it remains highly desirable to provide a water modifiable film having a substantial portion of thereof composed of a polyolefin. More desirably, the water modifiable film should have greater than about 55 weight percent of a polyolefin. When dry, the film should have the mechanical properties necessary for functionality. When wet, the films should lose at least a portion of its mechanical properties which would render the film flushable and transportable in a sewer system. Such films could be used for making flushable barrier films for personal care products.

It is therefore an object of the invention to provide a polyolefin-containing film that is water modifiable or water-degradable which contains higher levels of polyolefin content. More specifically, it is an object of the invention to provide a polyolefin-containing film having greater than about 55 weight percent of a polyolefin and less than about 45 weight percent of poly(ethylene oxide) that is water-modifiable or water degradable.

SUMMARY OF THE INVENTION

In its principal embodiment, the present invention provides a water-modifiable or water-degradable film comprising greater than about 55 weight percent of a modified polyolefin and less than about 45 weight percent of poly (ethylene oxide). The polyolefin is modified by having from about 0.1 weight percent to about 30 weight percent, based on the total weight of the polyolefin and poly(ethylene oxide), of a monomer grafted onto the polyolefin backbone. Preferably the monomer is 2-hydroxyethyl methacrylate or polyethylene glycol ethyl ether methacrylate. The film of the invention has a loss of at least 10% in two or more tensile properties selected from percent strain-to-break, peak stress, energy-to-break and modulus after being immersed in water for 30 seconds.

In an alternative embodiment, the present invention provides a flushable personal care article having a backing or barrier layer comprising a water-modifiable or water-degradable film comprising greater than about 55 weight percent of a modified polyolefin and less than about 45 weight percent of poly(ethylene oxide). The polyolefin is modified by having from about 0.1 weight percent to about 30 weight percent, based on the total weight of the polyolefin and poly(ethylene oxide), of a monomer grafted onto the polyolefin backbone. Preferably the monomer is 2-hydroxyethyl methacrylate or polyethylene glycol ethyl ether methacrylate. The film comprising the backing or barrier layer of the invention has a loss of at least 10% in two or more tensile properties selected from percent strain-to-break, peak stress, energy-to-break and modulus after being immersed in water for 30 seconds.

DETAILED DESCRIPTION OF THE INVENTION

As used herein "water modifiable" means that a four mil thick film (one mil equals 0.001 of an inch or 0.025 mm), when immersed in water for 30 seconds, will have modified by greater than 10% two or more of the following tensile properties: percent strain-to-break, peak stress, energy-to-break and modulus. To determine the degree of modification, the "wet" values are compared to the pre-immersed or "dry" film values.

The term "personal care product" or "personal care article" means articles such as infant diapers, sanitary napkins, adult incontinence garments, and the like.

By the term "backing layer" or "barrier layer" is meant that component of an infant diaper, sanitary napkin, adult incontinence garment or the like which is worn during normal use furthest from the user's body and which serves to minimize or prevent the exudation of the absorbed liquid.

Although the present invention is described with reference to a water modifiable film and, in particular, to personal care articles having a backing layer, liner, or barrier layer comprising such films, one skilled in the art will understand that the composition of the invention can be used to make other thermoplastic articles that can be extruded or injection molded in which the desired property of water degradability is needed such as packaging articles and the like.

The saturated ethylene polymers useful in the practice of this invention are homopolymers or copolymers of ethylene and polypropylene and are essentially linear in structure. As used herein, the term "saturated" refers to polymers which are fully saturated, but also includes polymers containing up to about 5% unsaturation. The homopolymers of ethylene include those prepared under either low pressure, i.e., linear low density or high density polyethylene, or high pressure, i.e., branched or low density polyethylene. The high density polyethylenes are generally characterized by a density that is about equal to or greater than 0.94 grams per cubic centimeter (g/cc). Generally, the high density polyethylenes useful as the base resin in the present invention have a density ranging from about 0.94 g/cc to about 0.97 g/cc. The polyethylenes can have a melt index, as measured at 2.16 kg and 190° C., ranging from about 0.005 decigrams per minute (dg/min) to 100 dg/min. Desirably, the polyethylene has a melt index of 0.01 dg/min to about 50 dg/min and more desirably of 0.05 dg/min to about 25 dg/min.

Alternatively, mixtures of various grades of polyethylene can be used as the base resin in producing the graft copolymer compositions, and such mixtures can have a melt index greater than 0.005 dg/min to less than about 100 dg/min.

The low density polyethylene has a density of less than 0.94 g/cc and are usually in the range of 0.91 g/cc to about 0.93 g/cc. The low density polyethylene has a melt index ranging from about 0.05 dg/min to about 100 dg/min and desirably from 0.05 dg/min to about 20 dg/min. Ultra low density polyethylene can be used in accordance with the present invention. Generally, ultra low density polyethylene has a density of less than 0.90 g/cc.

Generally, polypropylene has a semi-crystalline structure having a weight average molecular weight of about 40,000 or more, a density of about 0.90 g/cc, a melting point of 168 to 171° C. for isotactic polypropylene and a tensile strength of 5000 psi. Polypropylene can also have other tacticities including syndiotactic and atactic.

The above polyolefins can also be manufactured by using the well known multiple-site Ziegler-Natta catalyst or the more recent single-site metallocene catalysts. The metallocene catalyzed polyolefins have better controlled polymer microstructures than polyolefins manufactured using Ziegler-Natta catalysts, including narrower molecular weight distribution, co-momomer sequence length distribution, and stereoregularity. Metallocene catalysts are known to polymerize propylene into atactic, isotactic, syndiotactic, isotactic-atactic stereoblock copolymer.

Copolymers of ethylene which can be useful in the present invention may include copolymers of ethylene with one or more additional polymerizable, unsaturated monomers. Examples of such copolymers include, but are not limited to, copolymers of ethylene and alpha olefins (such as propylene, butene, hexene or octene) including linear low density polyethylene, copolymers of ethylene and vinyl esters of linear or branched carboxylic acids having 1–24 carbon atoms such as ethylene-vinyl acetate copolymers, and copolymers of ethylene and acrylic or methacrylic esters of linear, branched or cyclic alkanols having 1–28 carbon atoms. Examples of these latter copolymers include ethylene-alkyl (meth)acrylate copolymers, such as ethylene-methyl acrylate copolymers.

Poly(ethylene oxide) polymers suitable for use in the films of the invention are available from Union Carbide Corporation, Danbury, Conn. under the trade name of POLYOX®. Typically, poly(ethylene oxide) is a dry free flowing white powder having a crystalline melting point in the order of about 65° C., above which poly(ethylene oxide) resin becomes thermoplastic and can be formed by molding, extrusion and other methods known in the art.

In the principal embodiment of the invention, the water-modifiable film comprises greater than about 55 weight percent of a modified polyolefin and less than about 45 weight percent of unmodified poly(ethylene oxide). Desirably, the water modifiable film comprises from about 55 weight percent to about 85 weight percent of a modified polyolefin and from about 45 weight percent to about 15 weight percent of unmodified poly(ethylene oxide). More desirably, the water-modifiable film comprises from about 65 weight percent to about 85 weight percent of a modified polyolefin and from about 35 weight percent to about 15 weight percent of unmodified poly(ethylene oxide).

The polyolefin is modified by having grafted thereto from about 0.1 weight percent to about 30 weight percent, based on the weight of the polyolefin and poly(ethylene oxide), of a monomer. Desirably, the polyolefin is modified by having grafted thereto from about 1 weight percent to about 20 weight percent, and more desirably, from about 1 weight percent to about 10 weight percent, based on the weight of the polyolefin and poly(ethylene oxide), of a monomer. Preferred and thus exemplary monomers for graft-polymerization modification of the polyolefins include 2-hydroxyethyl methacrylate or polyethylene glycol ethyl ether methacrylate.

Generally, the modified polyolefin is made by feeding to an extruder an amount of polyolefin, monomer and a free radical initiator. The modified polyolefin and poly(ethylene oxide) is then melt blended in an extruder to form the water modifiable film. The method of making the modified polyolefin is described in greater detail in copending U.S. patent application Ser. No. 08/733,410 filed Oct. 18, 1996, allowed, entitled "Method of Making Polyolefins Having Greater Than 5 Percent 2-Hydroxyethyl Methacrylate Grafted Thereto", the entire disclosure of which is incorporated herein by reference. In accordance with this embodiment of the invention, suitable poly(ethylene oxide) polymers can have an average molecular weight ranging from 100,000 to about 8,000,000 gm/mole.

The free radical initiators which can be used to graft the monomer onto the polyolefin include acyl peroxides such as benzoyl peroxide; dialkyl; diaryl; or aralkyl peroxides such as di-t-butyl peroxide; dicumyl peroxide; cumyl butyl peroxide; 1,1-di-t-butyl peroxy-3,5,5-trimethylcyclohexane; 2,5-dimethyl-2,5-di(t-butylperoxy)hexane; 2,5-dimethyl-2, 5-bis-(t-butylperoxy)hexyne-3 and bis-(p-t-butyl peroxyisopropylbenzene); peroxyesters such as t-butyl peroxypivalate; t-butyl peroctoate; t-butyl perbenzoate; 2,5-dimethylhexyl-2,5-di(perbenzoate); t-butyl di-(per phthalate); dialkyl peroxymonocarbonates and peroxydicarbonates; hydroperoxides such as t-butyl hydroperoxide, p-menthane hydroperoxide, pinane hydroperoxide and cumene hydroperoxide and ketone peroxides such as cyclohexanone peroxide and methyl ethyl ketone peroxide. Azo compounds such as azo-bis-isobutyronitrile may also be used.

When modifying the polyolefin, the amount of free radical initiator added to the extruder should be an amount sufficient to graft from about 1 percent to 100 percent of the monomer onto the polymer, i.e., the polyolefin. This can range from about 0.1 weight percent to about 2 weight percent of initiator. Preferably, the amount of initiator added to the extruder ranges from about 0.1 weight percent to about 1 weight percent wherein all such ranges are based on the amount of monomer added to the melt blend.

The water-modifiable modified polyolefin-containing films of the present invention will, when immersed in water for about 30 seconds, have modified at least two of the tensile properties: percent stain-to-break, peak stress, energy-to-break and modulus by greater than 10%. Desirably, at least two of the tensile properties will be reduced greater than about 25%. More desirably, at least two of the tensile properties will be reduced from about 25% to about 98%, and even more desirably at least two of the tensile properties: percent stain-to-break, peak stress, energy-to-break and modulus will be reduced from about 30% to about 80%. The values in determining the extent of the tensile property or properties modification are relative to the dry condition, i.e. pre-immersion value for that measured property.

The present invention is illustrated in greater detail by the specific examples presented below. It is to be understood that these examples are illustrative embodiments and are not intended to be limiting of the invention, but rather are to be construed broadly within the scope and content of the appended claims.

COMPARATIVE EXAMPLE A

A 60/40 weight percent blend of low density polyethylene (PE) having a melt index of 1.9 decigrams per minute (dg/min) and a density of 0.922 grams per cubic centimeter (g/cc) (Dow 503I; available from Dow Chemical Company, Midland, Mich.) and poly(ethylene oxide) (PEO) having a molecular weight of 200,000 g/mol (POLYOX® WSRN-80 available from Union Carbide Corp., Danbury, Conn.) was fed to a Haake counter-rotating twin screw extruder at a rate of 5 lb/hr (2.27 kg/hr). The extruder had a length of 300 millimeters. Each conical screw had 30 millimeters diameter at the feed port and a diameter of 20 millimeters at the die. The extruder had four heating zones set at 170° C., 180° C., 180° C. and 190° C. The screw speed of the extruder was 150 rpm.

Film processing of all the blends was performed using a Haake extruder counter-rotating twin screw extruder as described above with the following modifications. The extruder included a 4 inch (101.6 mm) slit die at a temperature of 195° C. The screw speed was at 30 rpm. A chilled wind-up roll was used to collect the film. The chilled roll was operated at a speed sufficient to form a film having a thickness of about 4 mils (about 0.102 mm) and was maintained at a temperature of 15–20° C. Dry tensile tests were performed on a Sintech 1/D tensile tester available from MTS Systems Corp., Machesny Park, Ill. The film was cut into a type V dogbone shape in accordance with ASTM D638. The test was performed with a grip separation of 30 millimeters and a crosshead speed of 4 millimeters/second.

Wet tensile tests were performed on a Vitrodyne V1000 mini-tensile tester available from Chatillon, Greensboro, N.C. The film samples were placed in the grips and the testing apparatus was submerged in ambient temperature, non-stirred water for 30 seconds. The test was then run under the same conditions as the dry tensile test. Peak stress, percent strain-to-break, energy-to-break (as area under stress versus strain curve) and modulus were calculated using the actual stress versus strain values recorded from the tensile tester for each dry or wet tensile test. The peak stress was recorded as the greatest stress value. The percent stain-to-break was recorded as the percent strain value at break. The energy-to-break (area under stress versus stain curve) was calculated by the summation of rectangular "slices" under the curve determined for each strain value recorded from the tensile test, using the following formula:

$$((\text{Strain value}_x - \text{Strain value}_{x-1}) \times (\text{Stress value}_x + \text{Stress value}_{x-1}))/2$$

where 'X" is the sequential number of the slice. The modulus was calculated by linear regression of the initial region of the stress versus strain curve. The dry and wet properties of the film produced from the blend in Comparative Example A are indicated in Table 1 below.

TABLE 1

Loss in Tensile Properties Upon Wetting
Comparative Example A

| Property | Dry | Wet | Percent Loss from Dry to Wet |
|---|---|---|---|
| Thickness (mil) | 4.1 | 4.2 | |
| Percent Strain | 550 | 500 | 9 |
| Peak Stress (MPa) | 16.6 | 16.2 | 2 |
| Energy-to-Break ($\times 10^6$ J/m$^3$) | 65.7 | 64.0 | 3 |
| Modulus | 77.0 | 62.3 | 19 |

This example shows that a polymer blend of unmodified low density polyethylene with poly(ethylene oxide) having a weight average molecular weight of 200,000 is water resistant. The polymer blend was not water modifiable after 30 seconds of immersion in water.

EXAMPLES 1–3

For Examples 1–3, the low density polyethylene (Dow 5031) was modified by grafting thereto polyethylene glycol methacrylate (PEG-MA; available from Aldrich Chemical Company, Milwaukee, Wis.). A Haake extruder as described in Comparative Example A above was used. The extruder had four heating zones set at 170° C., 180° C., 180° C. and 190° C. The screw speed of the extruder was 150 rpm. The feed to the extruder comprised contemporaneously adding, at the extruder feed throat, 5 lb/hr (2.27 kg/hr) of polyethylene and the specified amounts of PEG-MA and free radical initiator ((2,5-dimethyl-2,5-di-(t-butylperoxy)hexane), supplied by Atochem, 2000 Market St., Philadelphia, Pa. under the tradename Lupersol® 101).

For Example 1 the PEG-MA feed rate was 0.125 lb/hr (0.057 kg/hr) and the initiator rate was 0.0125 lb/hr 0.057 kg/hr).

For Example 2 the PEG-MA feed rate was 0.25 lb/hr (0.114 kg/hr) and the initiator rate was 0.025 lb/hr (0.011 kg/hr).

For Example 3 the PEG-MA feed rate was 0.5 lb/hr (0.227 kg/hr) and the initiator rate was 0.025 lb/hr (0.011 kg/hr).

A film comprising a 60/40 weight percent blend of polyethylene and poly(ethylene oxide) was prepared following the procedure of Comparative Example A, except the modified polyethylene of each example was substituted for the unmodified polyethylene of Comparative Example A.

The dry and wet properties of the film produced from the blends in Examples 1–3 are indicated in Table 2 below.

In accordance with the invention, Examples 1–3 illustrate a water-modifiable or water-degradable film comprising a blend of a modified polyolefin comprising polyethylene with PEG-MA grafted thereto and unmodified poly(ethylene oxide). The films were water modifiable after 30 seconds of submersion in water.

TABLE 2

Loss in Tensile Properties Upon Wetting

| Example Property | 1 | | | 2 | | | 3 | | |
| --- | --- | --- | --- | --- | --- | --- | --- | --- | --- |
| | Dry | Wet | % Change | Dry | Wet | % Change | Dry | Wet | % Change |
| Thickness (mil) | 4.5 | 4.5 | 0 | 4.0 | 4.0 | 0 | 5.0 | 5.0 | 0 |
| Percent Strain-to-Break | 550 | 183 | 67 | 553 | 117 | 78 | 283 | 50 | 82 |
| Peak Stress (MPa) | 13.8 | 7.0 | 49 | 11.4 | 4.9 | 57 | 12.2 | 3.1 | 75 |
| Energy-to-Break ($\times 10^6$ J/m$^3$) | 54.5 | 11.2 | 80 | 46.0 | 4.0 | 91 | 27.5 | 0.8 | 97 |
| Modulus (Mpa) | 70.7 | 44.6 | 37 | 62.2 | 33.8 | 46 | 71.6 | 23.6 | 67 |

While the invention has been described with reference to the preferred embodiments and illustrated with regard to a range of optional features, those skilled in the art will appreciate that various substitutions, omissions, changes and modifications may be made without departing from the spirit of the invention as it is defined by the appended claims. Accordingly, it is intended that the foregoing description be deemed merely exemplary of the preferred scope of the present invention and not be deemed a limitation thereof.

We claim:

1. A polyolefin-containing film comprising greater than about 55 weight percent of a modified polyolefin and less than about 45 weight percent of unmodified poly(ethylene oxide) wherein said polyolefin is modified by grafting thereto from about 0.1 about 30 weight percent of a monomer, said film having a loss of at least 10% in two or more tensile properties selected from percent strain-to-break, peak stress, energy-to-break and modulus after being immersed in water for 30 seconds.

2. A film according to claim 1 wherein said film comprises from about 55 weight percent to about 85 weight percent of a modified polyolefin and from about 45 weight percent to about 15 weight percent of unmodified poly(ethylene oxide).

3. A film according to claim 2 wherein said film comprises from about 65 weight percent to about 85 weight percent of a modified polyolefin and from about 35 weight percent to about 15 weight percent of unmodified poly(ethylene oxide).

4. A film according to claim 1 wherein said polyolefin is polyethylene or propylene.

5. A film according to claim 2 wherein said polyolefin is polyethylene or propylene.

6. A film according to claim 3 wherein said polyolefin is polyethylene or propylene.

7. A film according to claim 1 wherein said modified polyolefin comprises from about 1 weight percent to about 20 weight percent of said monomer grafted onto said polyolefin, based on the total weight of the polyolefin and poly-(ethylene oxide) in said film.

8. A film according to claim 7 wherein said modified polyolefin has from about 1 weight percent to about 10 weight percent of said monomer grafted thereto, based on the total weight of the polyolefin and poly(ethylene oxide) in said film.

9. A film according to claim 1 wherein said monomer is selected from the group consisting of 2-hydroxyethyl methacrylate and polyethylene glycol ethyl ether methacrylate.

10. A film according to claim 1 wherein said monomer is selected from the group consisting of 2-hydroxyethyl methacrylate and polyethylene glycol ethyl ether methacrylate.

11. A film according to claim 7 wherein said monomer is selected from the group consisting of 2-hydroxyethyl methacrylate and polyethylene glycol ethyl ether methacrylate.

12. A film according to claim 8 wherein said monomer is selected from the group consisting of 2-hydroxyethyl methacrylate and polyethylene glycol ethyl ether methacrylate.

13. A film according to claim 1 wherein said loss in two or more of the tensile properties is greater than 25% after being immersed in water for 30 seconds.

14. A film according to claim 1 wherein said loss in two or more of the tensile properties is from about 25% to about 98% after being immersed in water for 30 seconds.

15. A film according to claim 1 wherein said loss in two or more of the tensile properties is from about 30% to about 80% after being immersed in water for 30 seconds.

16. A polyolefin-containing film comprising greater than about 55 weight percent of a modified polyolefin and less than about 45 weight percent of unmodified poly(ethylene oxide), said modified polyolefin comprising from about 0.1 weight percent to about 30 weight percent of a monomer grafted onto said polyolefin, based on the total weight of the polyolefin and poly(ethylene oxide) in said film, said monomer being selected from the group consisting of 2-hydroxyethyl methacrylate and polyethylene glycol ethyl ether methacrylate, and said film having a loss of at least 10 percent in two or more tensile properties selected from percent strain-to-break, peak stress, energy-to-break, and modulus after being immersed in water for 30 seconds.

17. A film according to claim 16 wherein said polyolefin is polyethylene or propylene.

18. A film according to claim 16 wherein said loss in two or more of the tensile properties is from about 30% to about 80% after being immersed in water for 30 seconds.

* * * * *

UNITED STATES PATENT AND TRADEMARK OFFICE
CERTIFICATE OF CORRECTION

PATENT NO.   : 6,111,014
DATED        : August 29, 2000
INVENTOR(S)  : James H. Wang et al.

It is certified that error appears in the above-identified patent and that said Letters Patent is hereby corrected as shown below:

<u>Column 4,</u>
Line 13, delete "co-momomer" and insert -- well controlled chemical composition distribution, co-monomer -- in place thereof.

<u>Column 7,</u>
Line 13, before "0.057" insert -- ( --;
Table 2, move the word "Example" up so that it is on the same line as "1", "2", and "3".

<u>Column 8,</u>
Line 2, after "0.1" insert -- to --.
Line 24, delete "7" and insert -- 1 -- in place thereof.

Signed and Sealed this

Tenth Day of September, 2002

Attest:

JAMES E. ROGAN
Attesting Officer    Director of the United States Patent and Trademark Office